(12) United States Patent
Fishman

(10) Patent No.: US 12,357,844 B2
(45) Date of Patent: Jul. 15, 2025

(54) INTENSITY MODULATED PIXELATED SUPERFICIAL RADIATION THERAPY SYSTEM AND METHOD

(71) Applicant: Skincure Oncology LLC, Burr Ridge, IL (US)

(72) Inventor: Kalman Fishman, Boca Raton, FL (US)

(73) Assignee: SKINCURE ONCOLOGY LLC, Burr Ridge, IL (US)

( * ) Notice: Subject to any disclaimer, the term of this patent is extended or adjusted under 35 U.S.C. 154(b) by 120 days.

(21) Appl. No.: 18/331,375

(22) Filed: Jun. 8, 2023

(65) Prior Publication Data

US 2023/0310885 A1 Oct. 5, 2023

Related U.S. Application Data

(63) Continuation-in-part of application No. 17/858,736, filed on Jul. 6, 2022, now Pat. No. 11,717,699.

(60) Provisional application No. 63/222,309, filed on Jul. 15, 2021.

(51) Int. Cl.
*A61N 5/10* (2006.01)
*A61B 90/00* (2016.01)
*A61B 6/00* (2006.01)

(52) U.S. Cl.
CPC ............ *A61N 5/1001* (2013.01); *A61B 90/37* (2016.02); *A61B 6/5247* (2013.01)

(58) Field of Classification Search
None
See application file for complete search history.

(56) References Cited

U.S. PATENT DOCUMENTS

| | | | |
|---|---|---|---|
| 6,654,443 B1 | 11/2003 | Hoffman | |
| 8,915,833 B1 | 12/2014 | Sahadevan | |
| 11,717,699 B2 * | 8/2023 | Fishman | ............... A61N 5/1001 |
| | | | 378/64 |
| 2006/0033044 A1 | 2/2006 | Gentry et al. | |
| 2008/0089480 A1 | 4/2008 | Gertner | |
| 2010/0260317 A1 | 10/2010 | Chang et al. | |

(Continued)

OTHER PUBLICATIONS

International Search Report issued in corresponding International Application No. PCT/US2022/36229, dated Nov. 8, 2022.

*Primary Examiner* — Hoon K Song
(74) *Attorney, Agent, or Firm* — McDermott Will & Emery LLP

(57) ABSTRACT

An x-ray treatment system includes an electron beam generator configured to generate an electron beam and an x-ray treatment head comprising an array of pixel source cells including side walls defining an x-ray transmissive interior. The side walls include an x-ray absorptive material. A target element is positioned to, when impacted by the electron beam, generate x-ray photon radiation within the x-ray transmissive pixel source cell interior. An electron beam control system includes a controller configured to control responsive to a treatment plan at least one of the direction and intensity of the electron beam to a particular one of the pixel source cells, and then responsive to the treatment plan to control at least one of the direction and intensity of the electron beam to at least one additional pixel source cell. A method of treating a patient with x-ray photon radiation is also disclosed.

16 Claims, 11 Drawing Sheets

(56) References Cited

U.S. PATENT DOCUMENTS

2011/0249787 A1 10/2011 Frey et al.
2012/0243667 A1 9/2012 Walters
2013/0182828 A1 7/2013 Watanabe et al.
2014/0177807 A1 6/2014 Lewellen et al.

* cited by examiner

US 12,357,844 B2

INTENSITY MODULATED PIXELATED SUPERFICIAL RADIATION THERAPY SYSTEM AND METHOD

FIELD OF THE INVENTION

The present disclosure relates generally to radiation therapy, and more particularly to x-ray photon radiation therapy systems and methods.

BACKGROUND OF THE INVENTION

Brachytherapy, including superficial radiation therapy, intra-operative radiation therapy, general brachytherapy, and Endocavitary radiation therapy, involves the use of radiation such as x-ray photons as a treatment to induce apoptosis in targeted cells, particularly skin cancer lesions, keloids, in-situ cancerous lesions, and other infected cells in the epidermis, dermis, subcutis, and other organs and tissue of the body. Care must be taken during the brachytherapy procedure to avoid damage to healthy cells. It is common during the administration of therapeutic x-ray photons to create a shielding template that is made of a highly x-ray absorptive material with a cutout portion to permit the passage of x-ray photons to the treated area only in the predefined areas exposed by the cutout. The fabrication of such templates is time consuming and imprecise. The cutout portion must be sized and contoured to allow the x-ray photons to strike the cells of the targeted lesion. Otherwise, not all of the targeted cancer cells will be eliminated. A treatment margin, sometimes as much as 20%, is therefore allowed in the template cutout design beyond the determined and targeted contours of the lesion to ensure that the entirety of the lesion is treated, while controlling, to some extent, the exposure of surrounding tissue to the treating beam. The creation of this treatment margin is subjective and complicated by the irregular surface and subsurface shapes of the lesion. Also, the template must be precisely placed and attached prior to treatment, and any movement of the template must be avoided.

SUMMARY

Aspects of the subject technology relate to an x-ray treatment system including an electron beam generator configured to generate an electron beam. The x-ray treatment system further includes an x-ray treatment head including a pixel source cell array including a plurality of pixel source cells. Each of the plurality of pixel source cells includes side walls defining an x-ray transmissive interior of the pixel source cell. The side walls include an x-ray absorptive material. The pixel source cells further include a target element that, when impacted by the electron beam, generates x-ray photon radiation within the x-ray transmissive interior. The x-ray treatment system also includes an electron beam control system that includes a controller. The controller is configured to receive a treatment plan for a treatment area to be treated. The controller is also configured to select, based on the received treatment plan, one or more pixel source cells out of the plurality of pixel source cells, the one or more pixel source cells depicting a shape of the treatment area. The controller is further configured to determine, based on the received treatment plan, at least one of a direction and intensity of the electron beam to be delivered to each of the selected one or more pixel source cells. The controller is also configured to transmit data to the electron beam generator and the x-ray treatment head, the data including the selected one or more pixel source cells and the determined at least one of the direction and the intensity for each of the selected one or more pixel source cells.

It is understood that other configurations of the subject technology will become readily apparent to those skilled in the art from the following detailed description, where various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

There are shown in the drawings embodiments that are presently preferred it being understood that the invention is not limited to the arrangements and instrumentalities shown, wherein.

DETAILED DESCRIPTION OF THE INVENTION

The detailed description set forth below is intended as a description of various configurations of the subject technology and is not intended to represent the only configurations in which the subject technology may be practiced. The appended drawings are incorporated herein and constitute a part of the detailed description. The detailed description may include specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

Figure 1:
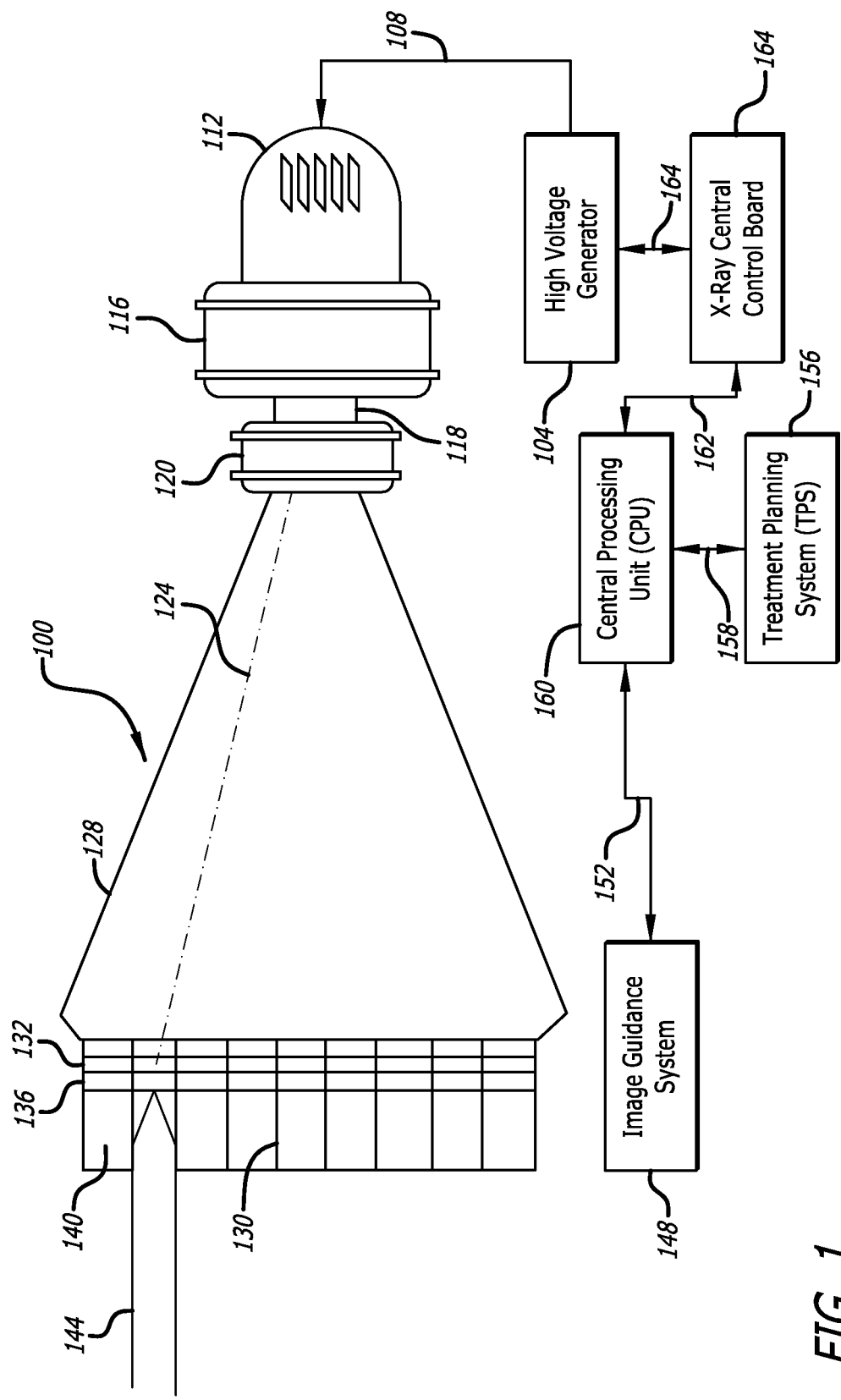
FIG. 1 is a schematic diagram of an example x-ray treatment system according to example aspects of the subject technology.

FIG. 1 illustrates a schematic diagram of an x-ray treatment system 100 according to example aspects of the subject technology. The x-ray treatment system 100 includes a high voltage generator 104, a line 108, an electron beam generator 112, a focusing electromagnetic coil 116, a vacuum drift tube 118, an electron beam steering electromagnetic coil 120, a pixel cell source array 126, and a vacuum jacket 128.

The high voltage generator 104 may communicate through the line 108 with the electron beam generator 112. The focusing electromagnetic coil 116 focuses the beam and passes the beam through the vacuum drift tube 118 to the electron beam steering electromagnetic coil 120 which steers the beam 124 to a desired location on the pixel cell source array 126. The vacuum jacket 128 is provided to allow the electron beam 124 to travel to the pixel cell source array 126 without attenuation by ambient air.

Figure 2:
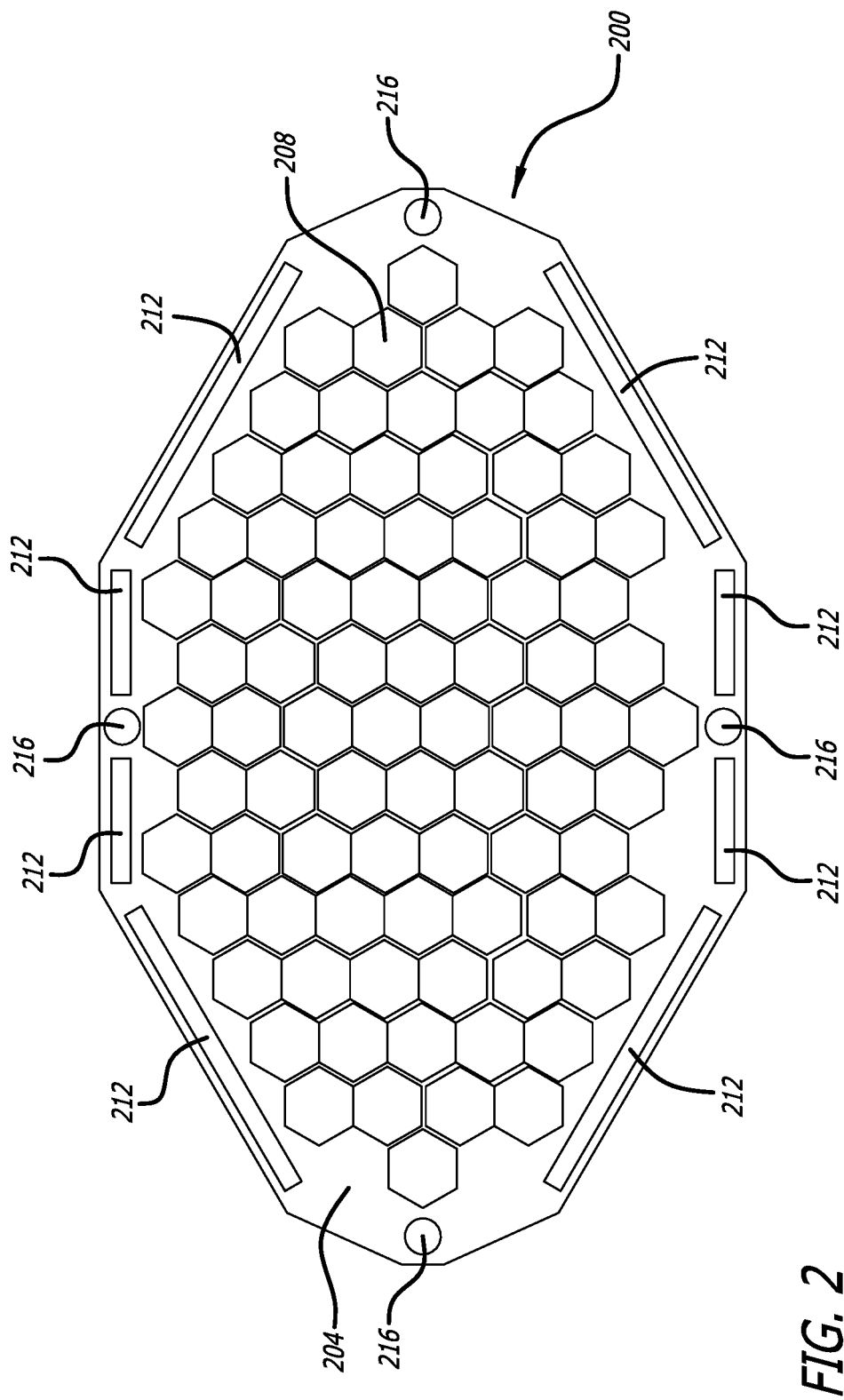
FIG. 2 is a front elevation of an example treatment head according to example aspects of the subject technology.

The pixel cell source array 126 may be provided on a treatment head (e.g., treatment head 200 in FIG. 2). The pixel cell source array 126 is comprised of individual pixel cells 130. The pixel source cell array 126 may be comprised of a plurality of single pixel source cells 130 attached together, or fabricated as a single monolithic structure, to form the treatment head geometry. The pixel source cell array 126 may be in various forms. Those forms include planar, curved, and contoured arrays.

The pixel source array 126 may have between 3 and 15,000 pixel source cells 130, ranging from 250 micrometer to 2 cm in diameter each. For example, the pixel source cell array 126 may have 3, 4, 5, 6, 7, 8, 9, 10, 20, 30, 40, 50, 60, 60, 80, 90, 100, 200, 300, 400, 500, 600, 700, 800, 900, 1000, 2000, 3000, 4000, 5000, 6000, 7000, 8000, 9000, 10000, 11000, 12000, 13000, 14000, or 15,000 pixel source cells 130, and can have a number of pixel source cells within a range of any low value and high value selected from these values. Each pixel source cell 130 may have a diameter of 0.25, 0.5, 0.75, 1, 2, 3, 4, 5, 6, 7, 8, 9, 10, 11, 12, 13, 14, 15, 16, 17, 18, 19, or 20 mm, and may have a diameter within a range of any high value and low value selected from these values.

The pixel source cell array 126 may be larger than the tumors to be treated. In cases where the tumor is larger than the pixel source cell array 126, the pixel source cell array 126 may be rastered and moved about in order to cover and encompass the entire lesion's or targeted tissue surface to be treated. The number and dimensions of the pixel source cells 130 may be dependent on the resolution that is desired, with higher numbers of pixel source cells 130 in a given area increasing the resolution and accuracy of the x-ray photon flux in covering the lesion contours while minimizing irradiation of healthy surrounding tissue. The pixel density of the pixel source cells 130 in the pixel source cell array 126 may be from 1 to 25 pixels per square inch. The length of each pixel source cell 130 may be from 1 mm to 100 cm. The dimensions of the pixel source cell array 126 may, therefore, vary. In one aspect, the overall pixel source cell array can have dimensions of from 1 $mm^2$ to 10 $cm^2$.

The pixel source cell array 126 may be large enough to irradiate the entirety of the lesion with x-ray photon flux emanating from the pixel source cell array 126. In some aspects, areas larger than the pixel source cell array 126 may be treated by rastering the pixel source cell array 126. The rastering of the pixel source cell array 126 may be performed by, for example, mounting the pixel source cell array 126 on a robotic arm and using appropriate locating fiducials.

Each of the pixel cells 130 of the pixel source cell array 126 includes a substrate 132, a target 136, and an open interior 140. The target 136 may be provided on the substrate 132 mounted within the open interior 140 of each of the pixel cells 130. For example, the electron beam 124 strikes the target 136 of a single pixel cell 130 or small group of pixel cells 130 to generate x-ray photons. The x-ray photons generated by the electron beam 124 striking the target 136 will be confined by the walls of the pixel cell 130 to provide a pixelated and constrained x-ray photon flux 144 that is aligned with the axis of the pixel cell 130.

The pixel source cells 130 may be individually targeted by the electron beam 124. In some instances, more than one pixel source cell 130 may be targeted at one time with the electron beam 124, however, this will be a subset of the total pixel source cells in the pixel source cell array. The pixel source cells 130 are not limited to the geometry illustrated in the drawings (FIGS. 1-4, 8, 9A, 9C, and 9E), and may have any suitable cross-sectional geometry. For example, the pixel source cells 130 may have a cross-sectional geometry comprising at least one selected from the group consisting of round, hexagonal, square, rectangular, triangular, pentagonal, octagonal, or heptagonal.

Any number of pixel source cells 130 can be incorporated into the array. The number, shape, and dimensions of the pixel source cells 130 are not limited to those illustrated in the drawings (e.g., FIGS. 1-4, 8, 9A, 9C, and 9E), and may vary according to clinical necessity and application.

The x-ray treatment system 100 further includes an image guidance system 148, a line 152, a treatment planning system (TPS) 156, a line 158, a central processing unit (CPU) 160, a line 162, an x-ray central control board 164, and a line 166. Each of the high voltage generator 104, the image guidance system 148, the TPS 156, the CPU 160, and the x-ray central control board 164 may represent an electronic device. The electronic device may include one or more programmable processors, one or more programmable logic circuitry, and/or one or more storage devices storing instructions related to processes and logic flows to be executed by the programmable processors and programable logic circuitry.

The image guidance system 148 communicates through the line 152 to the CPU 160. The CPU 160 communicates with the TPS 156 through the line 158. The CPU 160 also communicates with the x-ray central control board 164 through the line 162. The x-ray central control board 164 communicates with the high voltage generator 104 through the line 166. With the aid of the image guidance system 148, the x-ray treatment system 100 is configured to deliver accurate high-resolution intensity modulated pixelated x-ray beams to the targeted treatment area.

For example, the image guidance system 148 acquires one or more anatomical and/or topological images of the targeted treatment area, and sends the acquired image data to the CPU 160 through the line 152. The CPU 160 processes the image data and converts the image data. The CPU 160 sends the converted image data to the TPS 156 through the line 158, and subsequently, to the x-ray central control board 164 through the line 162. The image data may be comprised of more than one images of the targeted treatment area that are fused to form a hybrid image that combines the best features of the individual images. The one or more images may be acquired using different methodologies. For example, confocal microscopy imaging methodology may be optimal for imaging structural/functional features associated with a a first depth, and a second imaging methodology, such as photoacoustic microscopy, may be optimal for obtaining structural/functional features associated with a second depth. Additionally or alternatively, other types of imaging may also be combined, such as computerized tomography (CT) and magnetic resonance imaging (MRI).

The TPS 156 generates the treatment plan by embedding the image guidance data extracted from the acquired image of the designated treatment area from the image guidance system 148. The treatment plan is comprised of the image-guidance data, the activation sequence of the selected pixel source cells 130 in order to cover the targeted treatment area, the desired intensity of each pixel source cell 130, and the total treatment dose for the targeted treatment area (a function of activation time over target for each pixel source cell 130). The treatment plan is loaded onto the x-ray central control board 164 via the CPU 160.

The x-ray central control board 164 orchestrates and controls the x-ray treatment system 100 operational sequence. The x-ray central control board 164 controls the high voltage generator 104 based on the x-ray treatment system 100 operational sequence. When controlled by the x-ray central control board 164, the high voltage generator 104 sets the varying high voltage levels for each pixel source cell 130 in a treatment head (e.g., treatment head 200 of FIG. 2) while executing the treatment plan from the TPS 156.

For example, the x-ray central control board 164 controls the electron beam 124 generation and deflection towards each pixel source cell 130 selected per the treatment plan loaded from the TPS 156. The electron beam 124 travels towards the designated pixel source cell 130 through the vacuum chamber 128. The electron beam 124 is generated at a selected high voltage range by the high voltage generator 104 and transmitted through the high voltage line 108 to an electron gun cathode 112 for each pixel source cell 130 discretely, per the treatment plan loaded from the TPS 156.

The x-ray central control board 164 sets the electron beam focal size (diameter) by controlling the magnetic field intensity of the electron beam 124 using the focusing electromagnetic coil 116. The focused electron beam 124 is then passed onto the electron beam steering electromagnetic coil 120 through the vacuum drift tube 118. The electron beam steering electromagnetic coil 120 deflects the angle and vector of the electron beam 124 towards the selected pixel source cell 130 of the pixel source cell array 126 in the treatment head (e.g., treatment head 200 of FIG. 2). Upon hitting the x-ray target 136 encapsulated in the selected pixel source cell 130 and provided on a substrate 132, a collimated and well-defined x-ray photon flux emission occurs towards the designated treatment area. The collimation, x-ray beam geometry, and conformity are achieved by the high Z cell wall structure of pixel source 130. This sequence repeats itself for each designated and selected pixel source cell 130 in the treatment head (e.g., treatment head 200 in FIG. 2), per the treatment plan generated by the TPS 156 and the sequence control by the x-ray central control board 164. The manner of controlling the x-ray treatment system 100 is not limited to the method described herein, but may encompass modified method without from the scope of the subject technology.

The x-ray treatment system 100 includes an electron beam source configured to generate an electron vortex beam. An electron beam control system comprises a controller (e.g., image guidance system 148, CPU 160, TPS 156, x-ray central control board 164, high voltage generator 104) configured to control the electron beam generation system ((e.g., electron beam generator 112, a focusing electromagnetic coil 116, a vacuum drift tube 118, an electron beam steering electromagnetic coil 120) responsive to a treatment plan at least one of the direction and intensity of the electron beam to a particular one of the pixel source cells, and then responsive to the treatment plan to control at least one of the direction and intensity of the electron beam to at least one additional pixel source cell. The steering of the electron beam is commensurate with a treatment plan for a particular lesion treatment area.

The x-ray treatment system 100 employs a laser-based image guidance (e.g., image guidance system 148) such as confocal imaging to provide the treatment planning system (e.g., TPS 156) with the treated tumor or lesion surface and subcutaneous anatomical characteristics and topology, to better hone and plan the shape and intensity of the geometric arrangement of pixelated beam to better cover the entire surface and depth of the treated lesion or tumor, and to precisely plan the dose painting for each pixel source cell to more effectively treat the lesion or tumor.

The x-ray treatment system 100 allows individual energization of the pixel source cells 140 by controlling and steering of the electron beam, as shown in FIG. 1. The electron beam 124 may be controlled in order to focus and steer the electron beam 124 at very small tolerances, for example 100 um to 2 cm focal spot size range, and from 0.5 to 45 degree electron beam deflection range. Also, the energy of the beam may be individually controlled from one pixel source cell to another pixel source cell. Selective control of the beam energy for each pixel source cell allows for discrimination of the x-ray photon beam penetration at every single pixel source cell, and to modulate the dose between corresponding irradiated areas of the targeted treatment area as a function of beam on-time for each pixel source cell. Lesions have differing thicknesses and malignancy levels at various subcutaneous depths, and individualized pixel source cell control of the penetration and dose allows for increasing the efficacy and precision of the treatment for each targeted lesion and where more depth of penetration and intensified dose in the treatment area is desired. The x-ray treatment system 100 according to the present disclosure provides a novel capability to treat each lesion in a high precision and intensity, as required by the clinicians, instead of delivering an all-encompassing cohesive dose and treatment beam across the entire lesion, which is a compromise in most cases.

FIG. 2 illustrates a front elevation of a treatment head 200 according to example aspects of the subject technology. The treatment head 200 includes a housing 204 accommodating a pixelated x-ray source cell array 208, light sources 212, and laser beam emitters 216.

The shape of the housing 204 of the treatment head 200 is not limited to the shape illustrated in FIG. 2, but may be in other shapes. The pixelated x-ray cell source array 208 may include structures similar to or the same as those of the x-ray cell source array 126. The shape of the pixelated x-ray cell course array 208 may not be limited to the shape illustrated in FIG. 2. The number of x-ray cell sources in the pixelated x-ray cell source array 208 is not limited to the numbers of x-ray cell sources illustrated in FIG. 2, but may be fewer or greater.

The light sources 212 are provided in the perimeter of the front elevation of the treatment head 200. The light sources 212 include LED light sources that generate light to illuminate the targeted treatment area on a patient's body. The light sources 212 may also be used to allow the operator to see whether the pixelated x-ray cell source array 208 covers the targeted treatment area. The shape and the number of the light sources 212 are not limited to those illustrated in FIG. 2, but may include any shape or any number of the light sources 212 as long as the light sources 212 illuminate the targeted treatment area and allow the operator to see the coverage over the targeted treatment area.

The laser beam emitters 216 may create an accurate crosshair projection of the center point of the treatment head 200 to allow the operator to confirm proper and precise positioning and placement over the designated treatment area on the patient's body. The laser beam emitter 216 include four laser beam emitters, but the number of the laser beam emitters 216 may be fewer or more than four laser beam emitters illustrated in FIG. 2 as long as the laser beam emitters 216 can create the crosshair projection of the center point of the treatment head 200.

Figure 3A:
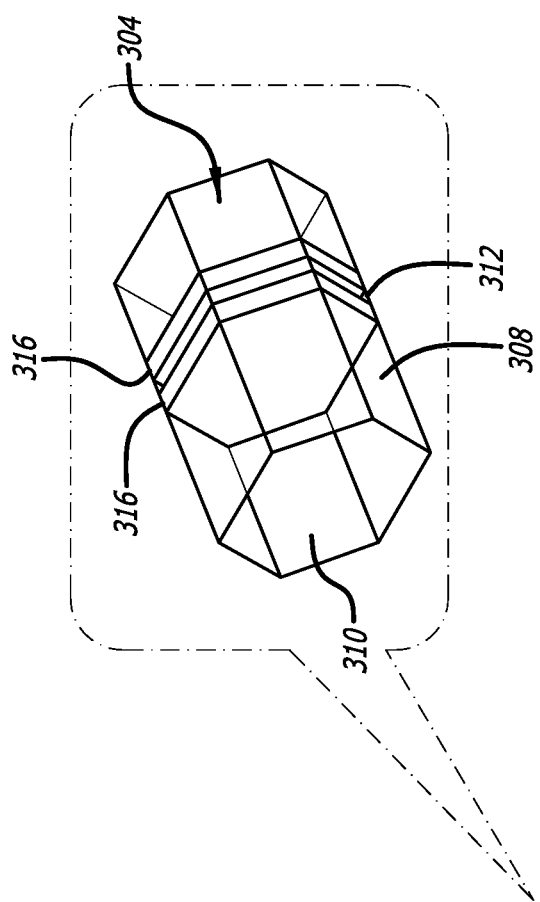
FIG. 3A is an expanded view, partially in phantom to reveal internal features of an example pixel source cell array according to example aspects of the subject technology.
Figure 3:
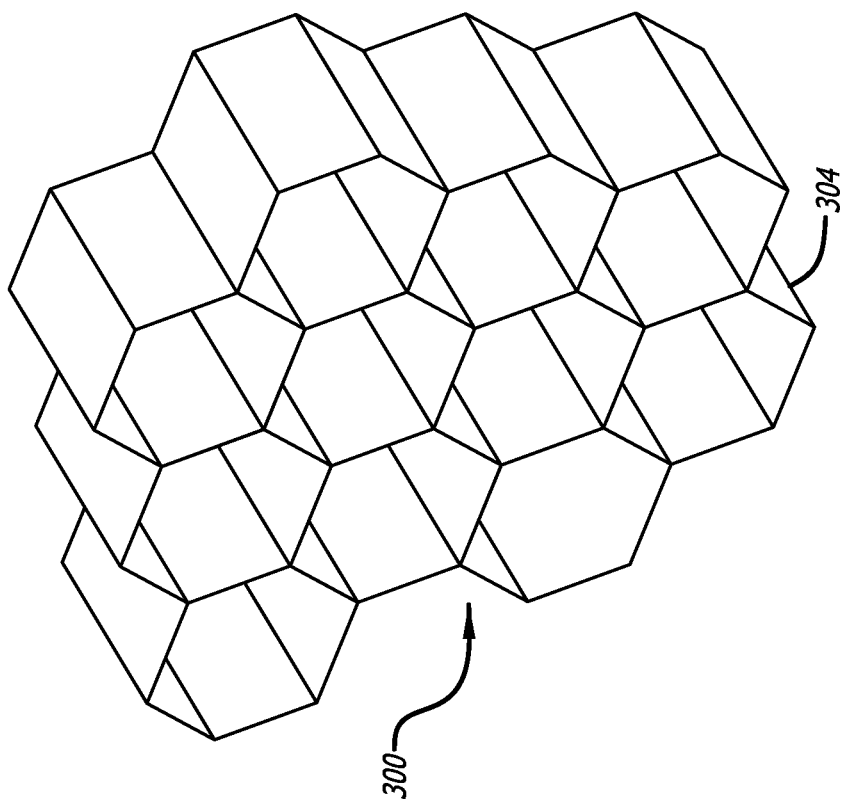
FIG. 3 is a perspective view of an example pixel source cell array according to example aspects of the subject technology.

FIG. 3 illustrates a perspective view of pixel source cell array 300 according to example aspects of the subject technology. The pixel source cell array 300 is comprised of a plurality of individual pixel source cells 304.

FIG. 3A illustrates an expanded view of one of the pixel source cells 304 of the pixel source cell array 300 according to example aspects of the subject technology. The pixel source cell 304 is shown partially in phantom to reveal internal features. Each pixel source cell 304 is comprised of x-ray absorbent walls 308, an x-ray transmissive interior 310, a target material 312, and one or more x-ray transmissive substrate layers 316.

The x-ray absorbent walls 308 define the x-ray transmissive interior 310. Within the x-ray transmissive interior 310 of the pixel source cell 304, a target material 312 and x-ray transmissive substrate layers 316 are provided such that the target material 312 is supported by the x-ray transmissive substrate layers 316.

The x-ray absorbent walls 308 comprise an x-ray absorptive material. For example, the x-ray absorptive material includes a high-Z material. The term high-Z material as used herein refers generally to materials which have an atomic number of at least 21. Suitable high-Z materials can be at least one selected from the group consisting of stainless steel, molybdenum (Mo), tungsten (W), and tantalum (Ta). Other x-ray absorptive materials are possible. The x-ray absorbent walls 308 constrain the x-ray photon flux within the pixel source cell such that a pixelated and constrained x-ray photon flux is generated by each pixel source cell.

The x-ray transmissive interior 310 defined by the x-ray absorbent walls 308 of each of the pixel source cells 304 may be open or filled or capped with an x-ray transmissive material (e.g., x-ray transmissive substrate layers 316). The x-ray transmissive substrate layers 316 must be transmissive to the electron beam targeted into the selected pixel source cell 304. When the x-ray transmissive substrate layers 316 are provided post the target element, the x-ray transmissive substrate layers 316 should be transmissive to the x-ray photon flux generated by the target material 312. The x-ray transmissive substrate layers 316 can be at least one selected form the group consisting of diamond, beryllium (Be), silicon carbide (SiC), sapphire, aluminum (Al), ceramic alumina ($Al_2O_3$), or boron nitride (BN). Other substrate materials that are transmissive to the electron beam may be used for the x-ray transmissive substrate layers 316.

The x-ray transmissive substrate layers 316 are provided in the x-ray transmissive interior 310 to support a target element (e.g., target material 312) to allow the target material 312 to generate x-ray photon radiation when the target material 312 is impacted by the electron beam. For example, the target material 312 may be supported by a single x-ray transmissive substrate layer 316. In some embodiments, the x-ray transmissive substrate layers 316 may support the target material 312 by sandwiching the target material 312 between two x-ray transmissive substrate layers 316. Yet in some other embodiments, the target element may be provided between two or more x-ray transmissive substrate layers 316.

The target material 312 may be positioned to be in contact with the x-ray absorbent walls 308 of the pixel source cell 304, such that the x-ray photons generated by the electron beam striking the target material 312 are emitted into and confined by the high-Z walls (e.g., x-ray absorbent walls 308) of the pixel source cell 304. The target material 312 may be positioned to receive the steered electron beam at the epicenter of target material 312, thereby generating the desired x-ray photon flux to be contained and collimated by the high-Z pixel source cell wall. For example, the target material 312 may be placed within the x-ray transmissive interior 310 defined by the x-ray absorbent walls 308. In some embodiments, the target material 312 may be placed at an end of the pixel source cell 304.

The target material 312 is formed of a material that responds to the electron beam with the generation of x-ray photons. Suitable target materials include, for example, molybdenum, gold or tungsten. Other materials which efficiently produce x-ray photons at relatively high efficiency when impacted by an electron beam may be used for the target material 312. The target element can be a single large target element that is associated with the entire pixel source cell array, or multiple pixel source cells clustered together. The target element can be discrete to each pixel source cell.

The pixel source cell 304 provides a confined and precise x-ray beam that covers a geometrically defined and limited surface area using the x-ray absorbent walls 308, the x-ray transmissive interior 310, the target material 312, and the x-ray transmissive substrate layers 316. The pixel source cell 304 accomplishes such technical improvements by directing a focused and steered electron beam towards the target material 312 that once hit by the steered electron beam, the x-ray photon flux generated by the target material 312 is confined by the high-Z walls, which collimates and directs the resulting x-ray photon beam towards a defined surface area (e.g., treatment area of a patient), without scattering beyond the pixel source cell's geometry. This further reduces the amount of healthy cells in the vicinity of the treatment area of the patient to be exposed to the x-ray. By providing a plurality of pixel source cells in an array, control of the steered electron beam can be used to generate a pre-determined shape and contour of the targeted treatment area in a pixelated fashion.

Figure 4:
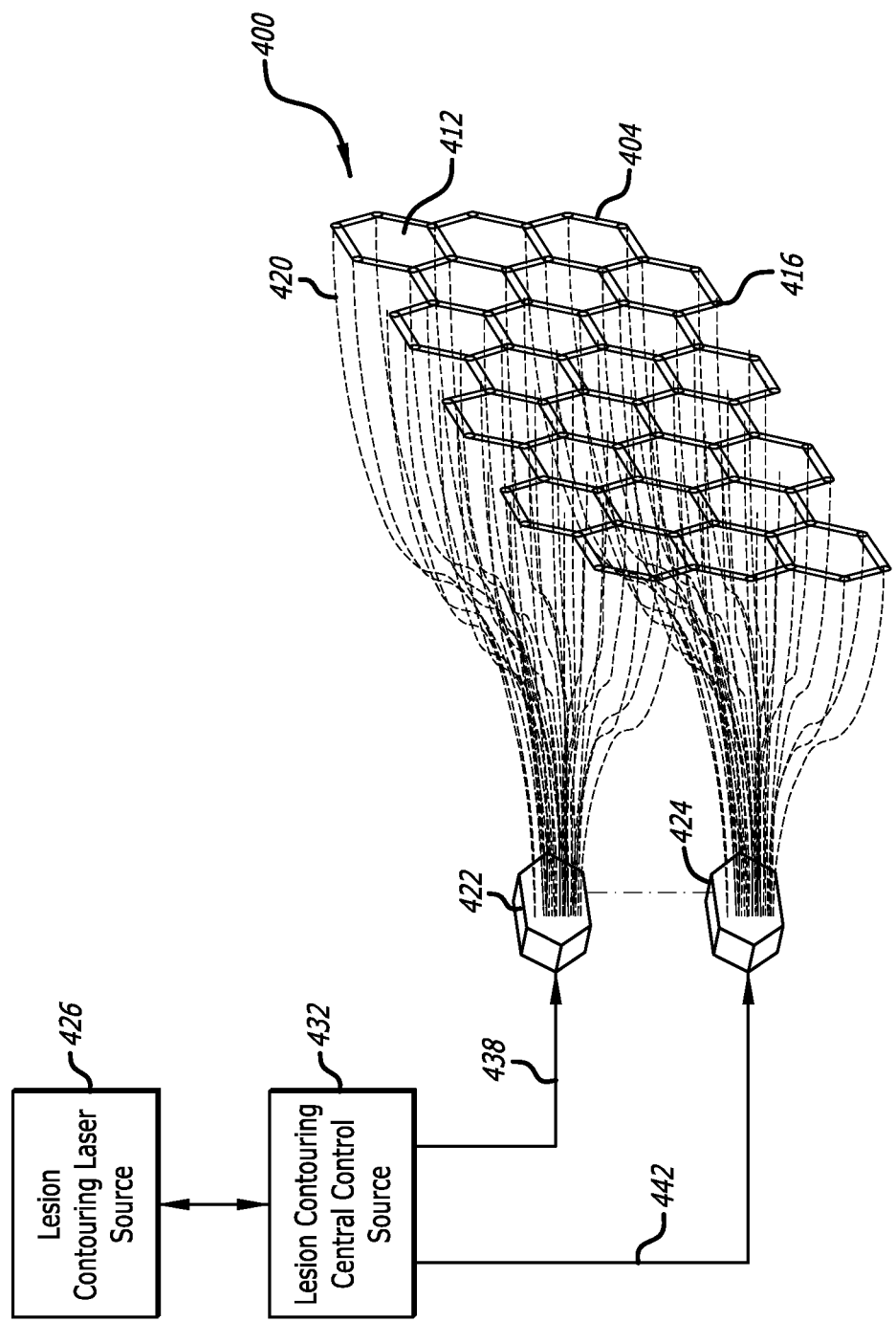
FIG. 4 is a perspective view of an example lesion contouring system for a pixel source cell array according to example aspects of the subject technology.

FIG. 4 illustrates a perspective view of a lesion contouring system 400 for a pixel source cell array according to example aspects of the subject technology. The lesion contouring system includes an array of pixel source cells 404, open interiors 412, fiber optic laser lights 416, fiber optic cables 420, one or more fiber optic cable clusters 422 and 424, a suitable lesion contouring laser source 426, a lesion contouring central control board 432, and connections 438 and 442.

The pixel source cells 404 include the open interiors 412, respectively. The open interior 412 allows the emission of x-ray photons generated by the target material (e.g., target materials 312 in FIG. 3). The fiber optic laser lights 416 is provided along the perimeter of each of the open interiors 412. The fiber optical laser lights 415 generate laser beams which are used to define the contours of the area to be irradiated by the x-ray photons emitted through the open interior 412 over the treatment area of the patient. The fiber optic laser lights 416 receive the laser light through the fiber optic cables 420. The fiber optic cables 420 may be bundled in one or more fiber optic cable clusters 422 and 424. The laser light is created by the suitable lesion contouring laser source 426. The lesion contouring central control board 432 directs, according to a treatment plan for the treatment area of the patient, the laser light to the bundle 422 through the connection 438, and to the bundle 424 through the connection 442, and thereby to the fiber optic cables 420 and fiber optic laser lights 416.

Providing the operator with an indication of the targeted x-ray beam's contour over the lesion (e.g., treatment area on the patient's body) allows the operator to verify the accurate placement and margins of the treating beam in real time over the actual lesion. This functionality is achieved by the lesion contouring module (e.g., lesion contouring system 400). The lesion contouring system 400 projects light such as laser to provide an indication of the head and pixel source cell array positioning to the operator. The fiber optic cluster of the lesion contouring system 400 may be comprised of a plurality of fiber optic strands which can be provided throughout the pixel source cell array, embedded in between the edges of each pixel source cell to indicate each pixel source cell's edge points, and individually controllable using the lesion contouring system 400, according to a treatment plan provided by the treatment planning system.

Figure 5:
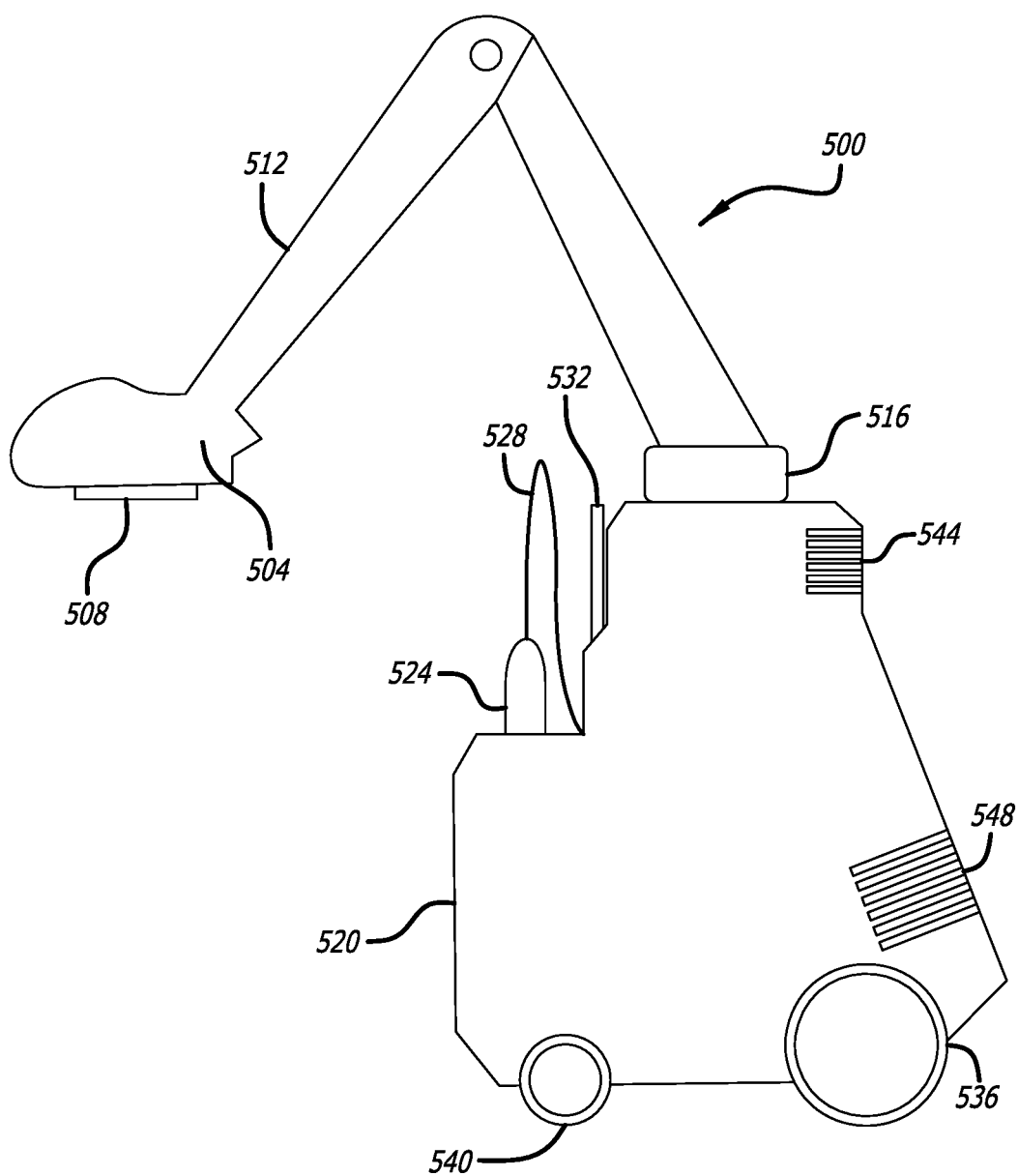
FIG. 5 is a side elevation of a mobile x-ray treatment system according to example aspects of the subject technology.

FIG. 5 illustrates a side view of a mobile x-ray treatment system 500 according to example aspects of the subject technology. The mobile x-ray treatment system 500 includes a treatment head 504, a pixel source cell array 508, an articulating arm assembly 512, a positioning motor 516, a mobile base support 520, a confocal imaging head 524, a confocal imaging head data and power cable 528, a treatment planning tablet 532, one or more base load casters 536, one or more base steering casters 540, a cold air intake louver 544, and a hot air exhaust louver 548.

The treatment head 504 includes the pixel source cell array 508. The structural relationship between the treatment head 504 and the pixel source cell array 508 may be similar to the structural relationship described using the treatment head 200 in FIG. 2. The pixel source cell array 508 may have the same or similar structure as any combination of the pixel source cell arrays described with respect to FIGS. 1-4. The treatment head 504 is mounted on one end of the articulating arm assembly 512. The other end of articulating arm assembly 512 is connected to the positioning motor 516. The positioning motor 516 is mounted on the mobile base support 520.

Articulating arm assembly 512 may be a robotic arm. The robotic arm allows controlled and registered positioning of the pixel source cell array 508. The robotic arm is articulated with appropriate robotic joints or articulation members under the control of the pixel source cell array 508. Additional articulations can also be provided different points of robotic arm to increase the number of degrees of freedom of placing, orienting and moving treatment head. The robotic arm is advantageously selected to be a robotic system that provides freedom of movement about multiple orthogonal axes (e.g. up to seven axes) and includes lightweight force and torque sensors (not shown) to ensure safe operation with humans without the need for a safety fence. Exemplary robots of this kind are commercially available from various sources. Communications, control, and power lines may extend from the base of the robotic arm to the pixel source cell array 508 located at the end of the robotic arm.

The robotic arm can facilitate constant position of the pixel source cell array 508 in relation to the patient. The robotic arm can facilitate controlled movement of pixel source cell array 508 during treatment of the patient in response to autonomic motions of the patient associated with breathing and the like. Such motion control can be facilitated by use of force sensors disposed in the robotic arm, or by means of fiducial markers disposed on the patient to track such movements. The robotic arm can automatically move the pixel source cell array 508 to provide a more uniform treatment. The robotic arm may also automatically account for, or cancel, the weight, momentum, and/or torque of the pixel source cell array 508 such that manual movement of the pixel source cell array 508 will require less effort by an operator.

Additionally or alternatively, the robotic arm may include a hand component on the end of the arm to allow the arm to pickup and utilize multiple components during the treatment of a patient. The multiple components may include, for example, the pixel source cell array 508 and confocal imaging head 524. During treatment, the hand component of the robotic arm may automatically pickup the confocal imaging head 524 to acquire an image of the area to be treated, securely park the confocal imaging head 524 after use, and then pickup the pixel source cell array 508 to deliver treatment to the patient as described herein.

Although not illustrated in FIG. 5, the mobile base support 520 may include an image guidance system (e.g., image guidance system 148 of FIG. 1), a CPU (e.g., CPU 160 of FIG. 1), a TPS (e.g., TPS 156 of FIG. 1), an x-ray central control board (e.g., x-ray central control board 164 of FIG. 1), and a high voltage generator (e.g., high voltage generator 104 of FIG. 1). The mobile base support 520 further includes the confocal imaging head 524 which is connected to the mobile base support 520 via the confocal imaging head data and power cable 528. For example, the confocal imaging head 524 may be part of the image guidance system, and is used to acquire one or more anatomical and/or topological images of the treatment area of the patient's body. The acquired one or more anatomical and/or topological images are transmitted to the CPU in the mobile base support 520 via the confocal imaging head data and power cable 528.

The mobile base support 520 further includes the treatment planning tablet 532 attached thereto. The treatment planning tablet 532 is a user interface that allows the operator to review the one or more anatomical and/or topological images and input data and instructions (e.g., treatment plan) for controlling the treatment head 504. For example, the treatment planning tablet 532 may be part of the TPS, and receives the acquired one or more anatomical and/or topological images from the CPU. The received one or more anatomical and/or topological images may be displayed on the treatment planning tablet 532 for review by the operator. The treatment planning tablet 532 may receive user input from the operator to generate a treatment plan based at least on the received one or more anatomical and/or topological images. The generated treatment plan is transmitted from the treatment planning tablet 532 to the x-ray central control board via the CPU. Based on the received treatment plan, the x-ray central control board selects one or more pixel source cells (not illustrated) out of the pixel source cell array 508 that covers the treatment area and determines the intensity of the x-ray beam to be delivered to each of the selected one or more pixel source cells. Then, the x-ray central control board communicates the selected one or more pixel source cells and the corresponding intensities of the x-ray beam to the high voltage generator. Based on the communication from the x-ray central control board, the high voltage generator then communicates with the treatment head 504 and the pixel source cell array 508 to deliver accurate high-resolution intensity modulated pixelated x-ray beams to the targeted treatment area.

The mobile base support 520 may further include the base load casters 536 and the base steering casters 540 to allow the operator to move the mobile x-ray treatment system 500 to places as needed. The mobile base support 520 may further include a locking system (not shown) to securely park the mobile x-ray treatment system 500. The locking system may be hands free to allow the operator to easily activate the locking system, such as with the operator's foot. The mobile base support 520 further includes the cold air intake louver 514 and the hot air exhaust louver 548 to supply cooling air to the mobile x-ray treatment system 500.

In some embodiments, the x-ray treatment system 500 may be comprised of several interchangeable treatment heads, which differ from each other by size, number of pixel source cells in the array, the shape of the entire array, the shape and dimensions of each pixel source cell, the axis of each pixel source cell and thus the direction of the x-ray photon flux emanating from each pixel source cell, and the arrangement of all pixel source cells in the array.

Figure 6:
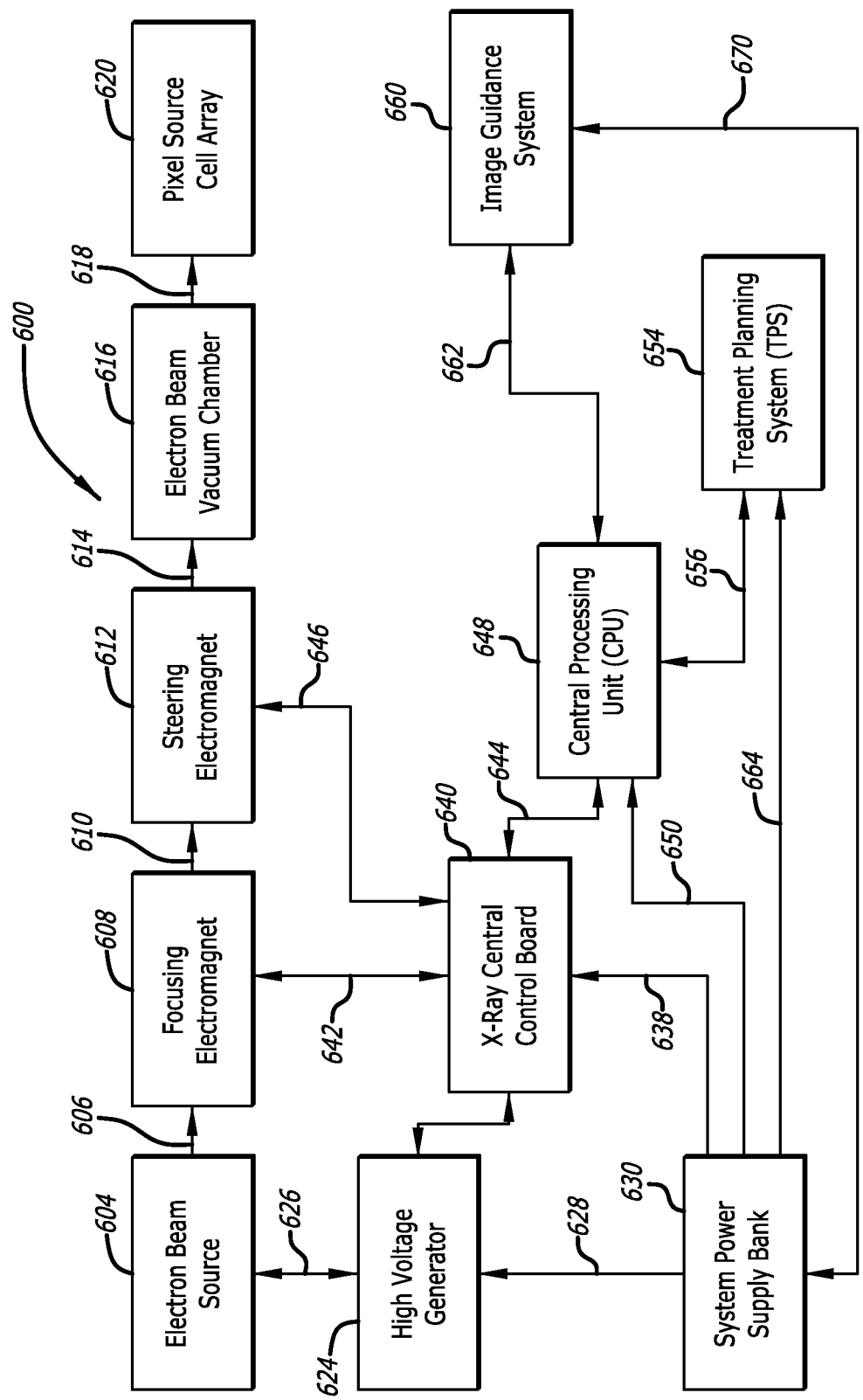
FIG. 6 is a block diagram of the components of an example x-ray treatment system according to example aspects of the subject technology.

FIG. 6 a block diagram of the components of an x-ray treatment system 600 according to example aspects of the subject technology. Specifically, the block diagram shows the components of the x-ray treatment system 600 and a flow of the method for controlling the x-ray treatment system 600 according to example aspects of the subject technology.

The x-ray treatment system 600 includes an electron beam source 604, an electron beam 606, a focusing electromagnet 608, a focused electron beam 610, a steering electromagnet 612, a directed electron beam 614, an electron beam vacuum chamber 616, an electron beam 618, a pixel source cell array 620, a high voltage generator 624, a connection 626, a system power supply bank 630, a power line 628, a x-ray central control board 640, a power line 638, a connection 642, a connection 644, a connection 646, a CPU 648, a power line 650, a TPS 654, a connection 656, an image guidance system 660, a connection 662, a power line 664, and a power line 670. The connections 626, 642, 644, 646, and 656 may provide bi-directional communication between two components.

The system power supply bank 630 provides power to the high voltage generator 624 via the power line 628, the x-ray central control board 640 via the power line 638, the CPU 648 via the power line 650, the TPS 654 via the power line 664, and the image guidance system 660 via the power line 670. The high-voltage generator 624 supplies power to the electron beam source 604 through the connection 626.

The image guidance system 660 acquires one or more anatomical and/or topological images of the treatment area (e.g., lesion) of the patient's body, and generates image guidance data based on the acquired one or more anatomical and/or topological images. The image guidance data is communicated to the CPU 648 via the connection 662. The CPU 648 also receives and provides information to an image guidance system 660 through the connection 662. The CPU 648 communicates the image guidance data to the TPS 654 via the connection 656. The TPS 654 generates a treatment plan based on the image guidance data. The generated treatment plan is communicated back to the CPU 648 via the connection 656. The CPU 648 generates instructions for controlling the electron beam source 604, the focusing electromagnet 608, and the steering electromagnet 612 based on the treatment plan, and communicates the instructions to the x-ray central control board 640 via the connection 644.

The x-ray central control board 640 processes these instructions and provides control signals to the focusing electromagnet 608 through the connection 642 and to the steering electromagnet 612 through the connection 646. The x-ray central control board 640 further provides control signals to the high voltage generator 624. The high voltage generator 624 provides the high voltage gain for the electron beam source 604 via the connection 626 based on the control signals received from the x-ray central control board 640.

The electron beam source 604 generates the electron beam 606 based on the control signals received from the x-ray central control board 640. That is, the electron beam generation and control in the electron beam source 604 are managed by the x-ray central control board 640 based on the treatment plan generated by the TPS 654. The electron beam 606 passes through the focusing electromagnet 608 which generates the focused electron beam 610. The focused electron beam 610 then enters the steering electromagnet 612. the directed electron beam 614 emerges and enters the electron beam vacuum chamber 616. The electron beam 618 then strikes the pixel source cell array 620, from which intensity modulated pixelated x-ray photon beams are generated to treat the lesion (e.g., treatment area). The CPU 648 operates and manages the x-ray treatment system 600 on a high level by controlling the system's modules, signals, and operational sequences.

Figure 7:
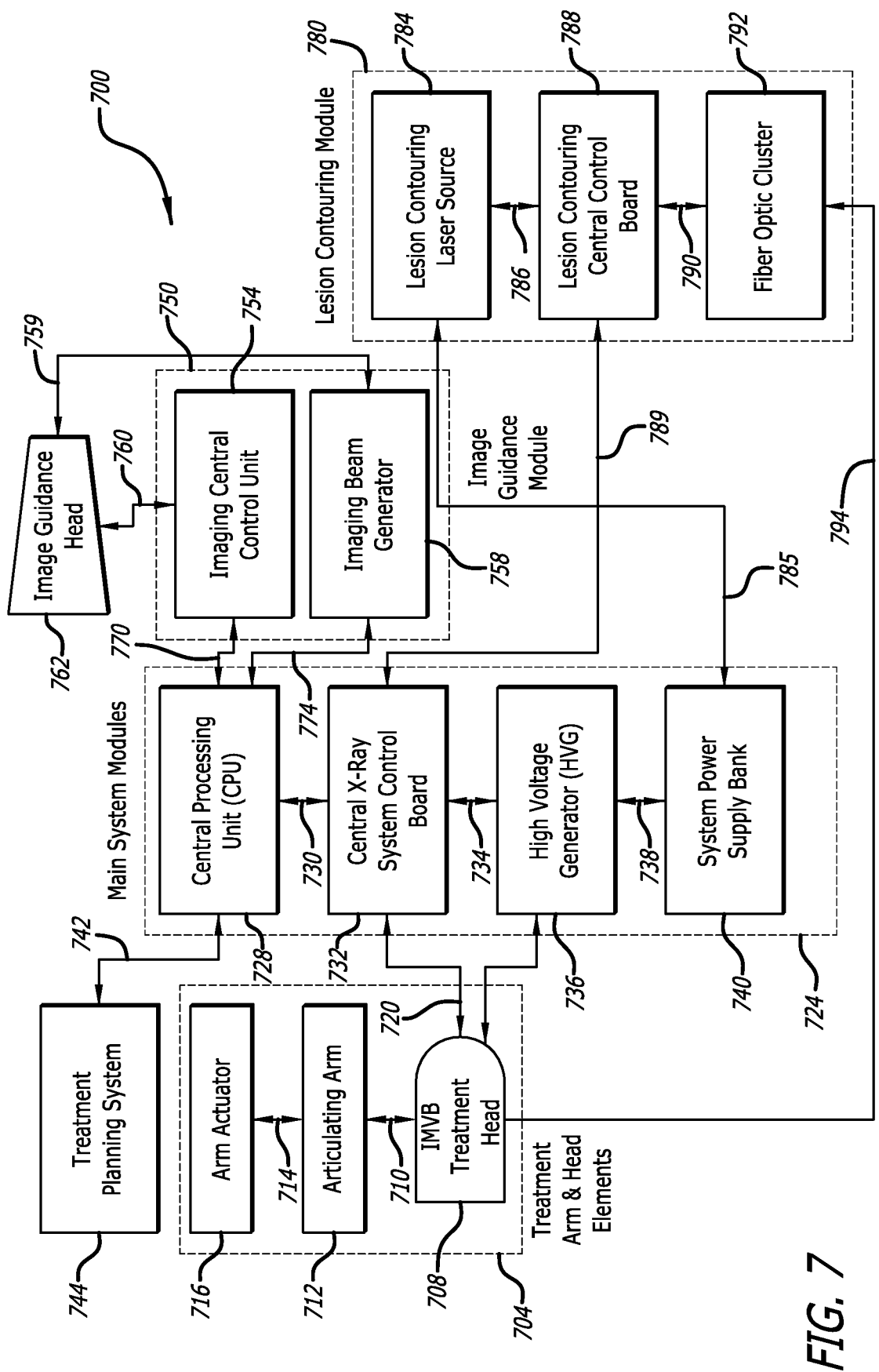
FIG. 7 is a block diagram illustrating an example method of performing x-ray therapy according to example aspects of the subject technology.

FIG. 7 illustrates a block diagram illustrating a method for performing x-ray therapy an intensity modulated pixelated superficial radiation therapy system 700 according to example aspects of the subject technology. The system 700 includes a treatment arm and head element control system 704, main system control modules 724, a TPS 744 (e.g., TPS 156 of FIG. 1, treatment planning tablet 532 of FIG. 5, TPS 654 of FIG. 6), an image guidance module 750 (e.g., image guidance system 148 of FIG. 1, image guidance system 660 of FIG. 6), an image guidance head 762 (e.g., confocal imaging head 524 of FIG. 5) connected and controlled by the image guidance module 750, and a lesion contouring module 780 (e.g., lesion contouring system 400 of FIG. 4).

The image guidance module 750 includes an imaging central control unit 754 and an imaging beam generator 758. The imaging central control unit 754 is connected to the image guidance head 762 via a connection 760 and to the imaging beam generator via a connection 759. For example, the image guidance head 762 receives, from the imaging beam generator 758 via the connection 759, the imaging beam required to acquire one or more anatomical and/or topological images of the treatment area (e.g., lesion) of the patient. The acquired one or more anatomical and/or topological images are transmitted to the imaging central control unit 754 from the image guidance head 762 via the connection 760. The imaging central control unit 754 communicates image guidance data of the acquired one or more anatomical and/or topological images to a CPU 728 of the main system modules 724 via a connection 770. The imaging beam generator 758 may receive instructions for controlling the image guidance head 762 from the CPU 728 of the main system modules 724 via a connection 774.

The main system modules 724 include the CPU 728 (e.g., CPU 160 of FIG. 1, CPU 648 of FIG. 6), a central xc-ray system control board 732 (e.g., x-ray central control board 164 of FIG. 1), a high voltage generator (HVG) 736 (e.g., high voltage generator 104 of FIG. 1, high voltage generator 624 of FIG. 6), and a system power supply bank 740 (e.g., system power supply bank 630 of FIG. 6). The CPU 728 is connected to the central x-ray system control board 732 via a connection 730. The central x-ray system control board 732 is connected to the HVG 736 via a connection 734. The HVG connected to the system power supply bank 740 via a connection 738. The system power supply bank 740 provides power to the system 700.

Upon receiving the image guidance data from the imaging central control unit 754, the CPU 728 transmits imaging guidance data to the TPS 744 via a connection 742. The TPS 744 may provide the image guidance data to the operator of the system 700. For example, the TPS 744 may include a display (not illustrated) for displaying the image guidance data and a user interface (not illustrated) for receiving user inputs from the operator. In some embodiments, the display may be a touchscreen acting as the user interface. The TPS 744 may receive, from the operator via the user interface, a treatment plan for the treatment area of the patient imaged by the image guidance head 762. The TPS 744 transmits the treatment plan to the CPU 728.

When the CPU 728 receives the treatment plan from the TPS 744, the CPU 728 selects, based on the received treatment plan, one or more pixel source cells out of the pixel source cell array (not illustrated) in the IMVB treatment head 708 to be used to emit the x-ray through to the treatment area. The CPU 728 determines, based on the treatment plan, the intensity of the x-ray for each of the selected one or more pixel source cells. The CPU 728 may further determine the angles and/or directions of the emission of the x-ray. The CPU 728 transmits control signals corresponding to the selected one or more pixel source cells, the corresponding intensities of the x-ray, and the angles and/or direction of the emission of the x-ray to the central x-ray system control board 732 via the connection 730.

The central x-ray system control board 732 transmits the control signals to the high voltage generator 736 via the connection 734, the IMVB treatment head 708 via the connection 720, and a lesion contouring central control board 788 of the lesion contouring module 780 via a connection 789.

Upon receiving the control signals from the central x-ray system control board 732, the high voltage generator 736 determines the high voltage gain based on the received control signals, and provides the determined high voltage gain to an electron beam source (not illustrated) in IMVB treatment head 708.

The lesion contouring module 780 includes a lesion contouring laser source 784, the lesion contouring central control board 788, and a fiber optic cluster 792. The lesion contouring laser source 784 is connected to the lesion contouring central control board 788 via a connection 786. The lesion contouring central control board 788 is connected to the fiber optic cluster 792 via a connection 790.

The fiber optic cluster 792 includes a plurality of fiber optic cables (not illustrated) connected to the IMVB treatment head 708 via a connection 794. The lesion contouring laser source 784 receives power from the system power supply bank 740 via a connection 785. The lesion contouring laser source 784 provides laser light to the plurality of fiber optic cable. Based on the control signals received from the central x-ray system control board 732, the lesion contouring central control board 788 selects one or more fiber optic cables out of the plurality of fiber optic cables for transmitting the laser light therethrough.

The treatment arm and head element control system 704 includes the IMVB treatment head 708, an articulating arm 712, and an arm actuator 716. The treatment head 708 is connected to the articulating arm 712 via a connection 710. The articulating arm 712 is connected to the arm actuator 716 via connection 714.

Although not illustrated in FIG. 7, the IMVB treatment head 708 may include a pixel source cell array (e.g., pixel source cell array 126 of FIG. 1, pixelated x-ray source cell array 208 of FIG. 2, pixel source cell array 300 of FIG. 3, pixel source cell array 508 of FIG. 5, pixel source cell array 620 of FIG. 6). The one or more pixel source cells that are selected based on the treatment plan out of the pixel source cell array in the IMVB treatment head 708 may receive electron beams from the high voltage generator 736. For example, the intensity of the electron beam delivered to each of the selected one or more pixel source cells may be set based on the treatment plan. In some embodiments, the intensities may be even across the one or more pixel source cells. In some other embodiments, the intensities may vary from one pixel source cell to another. Yet in some other embodiments, the same intensity may be delivered to some of the one or more pixel source cells while a different intensity may be delivered to other of the one or more pixel source cells.

The IMVB treatment head 708 may further include fiber optic laser lights (e.g., fiber optic laser lights 416 of FIG. 4) (not illustrated). One or more fiber optic laser lights corresponding to the selected one or more of fiber optic cables may receive laser lights from the lesion contouring laser source 784. The one or more fiber optic laser lights form a contour representing the perimeter of an area to be irradiated with the x-ray over the treatment area of the patient.

The articulating arm 712 (e.g., articulating arm assembly 512 of FIG. 5) may be controlled by the arm actuator 716 according to the control signals received from the central x-ray system control board 732 such that the IMVB treatment 708 is positioned over the treatment area of the patient.

Figure 8:
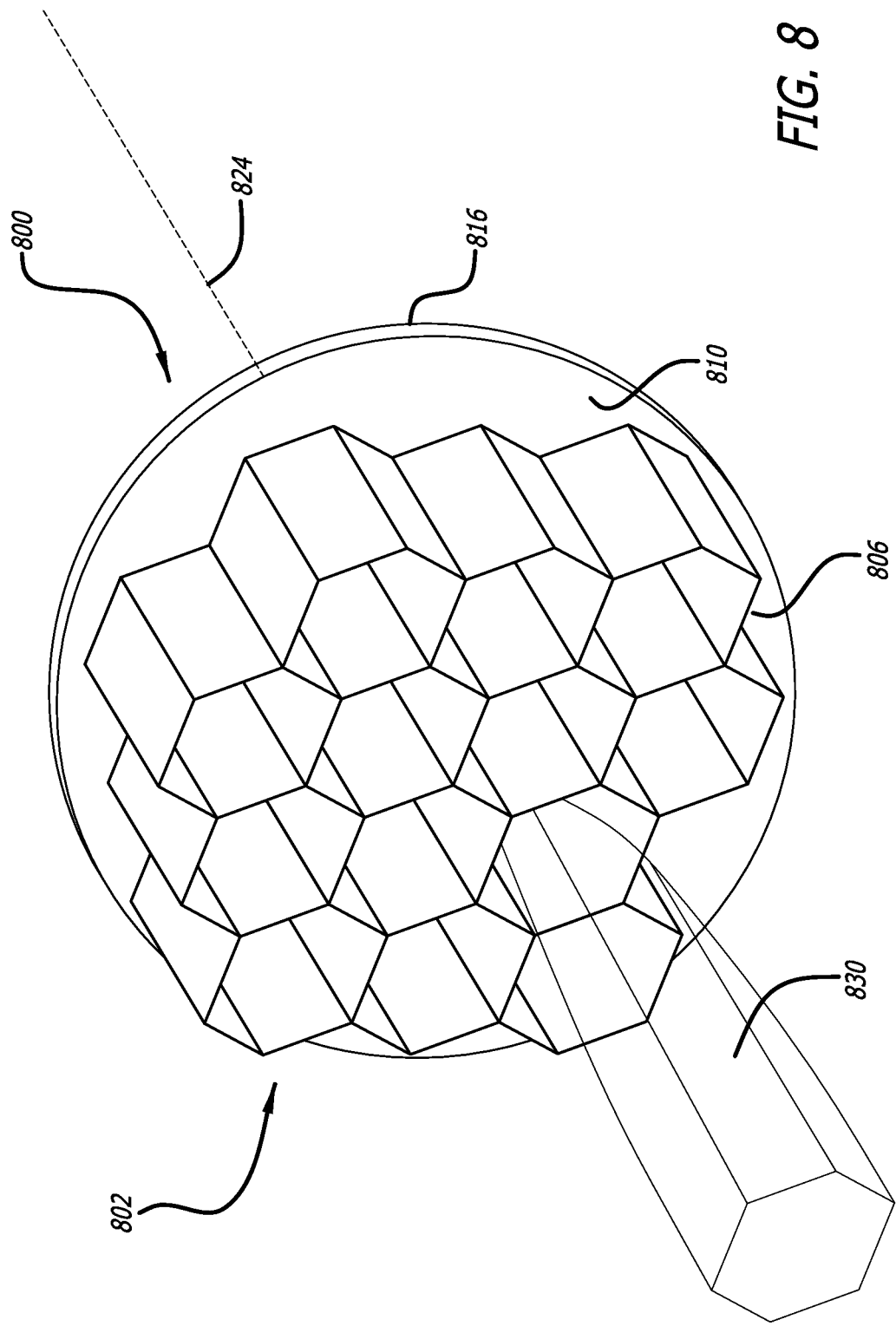
FIG. 8 is a schematic perspective view of an alternative embodiment of a pixel source cell array according to example aspects of the subject technology.

FIG. 8 illustrates a schematic perspective view of an alternative embodiment of a pixel source cell array 802 of a treatment head 800 according to example aspects of the subject technology. The treatment head 800 includes the pixel source cell array 802 comprised of individual pixel source cells 806. The pixel source cell array 802 is mounted to a target material 810. The target material 810 may include materials such as molybdenum, gold or tungsten. The target material 810 may be mounted on a suitable target substrate 816. The suitable target substrate 816 may include materials such as diamond, beryllium (Be), silicon carbide (SiC), sapphire, aluminum (Al), ceramic alumina ($Al_2O_3$), or boron nitride (BN). Other substrate materials are possible. A focused and steered electron beam 824 strikes the target material 810. In response to the focused and steered electron beam 824 striking the target material 810, x-ray photons may be generated. The x-ray photons generated from the target material 810 are confined by the walls of the individual pixel source cells 806 and a constrained x-ray photon flux 830 is produced. The x-ray photon flux 830 then irradiates the treatment area of the patient.

Figure 9B:
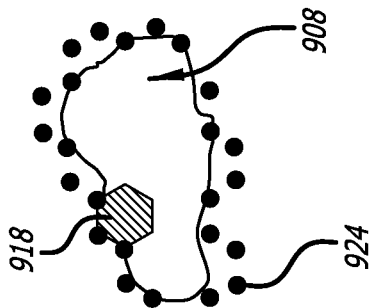
FIG. 9B is a schematic depiction of a lesion being treated in the first stage according to example aspects of the subject technology.
Figure 9D:
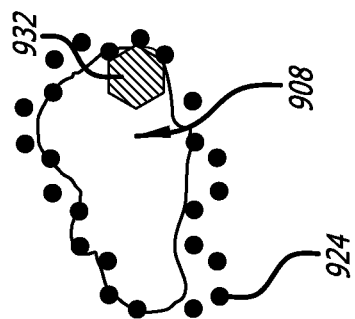
FIG. 9D is a schematic depiction of the lesion being treated in the second stage according to example aspects of the subject technology.
Figure 9A:
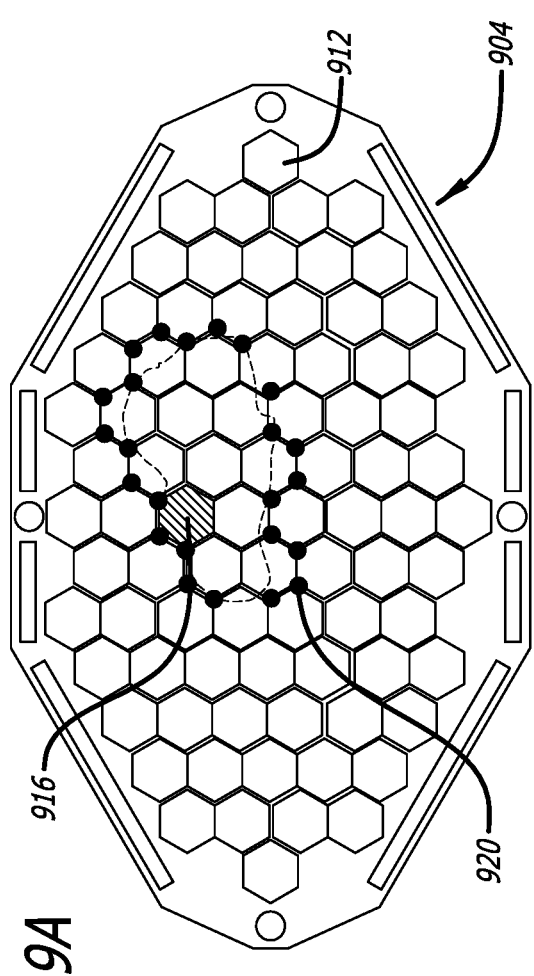
FIG. 9A is a schematic diagram of a treatment head in a first stage of operation according to example aspects of the subject technology.
Figure 9C:
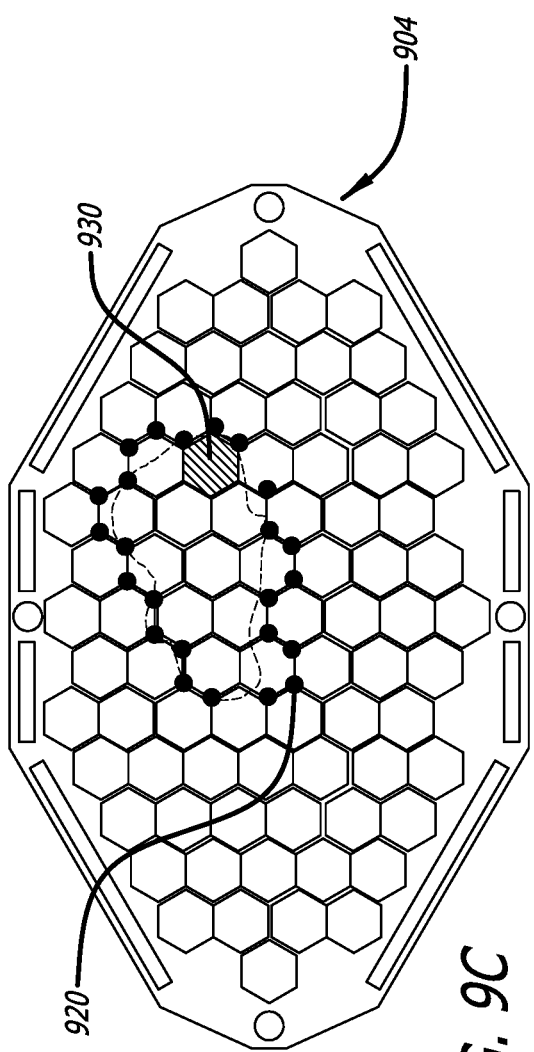
FIG. 9C is a schematic diagram of the treatment head in a second stage of operation according to example aspects of the subject technology.
Figure 9F:
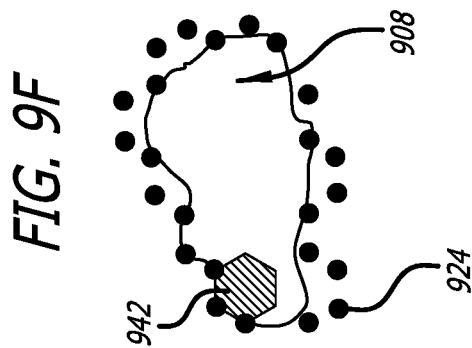
FIG. 9F is a schematic depiction of the lesion being treated in the third stage according to example aspects of the subject technology.
Figure 9E:
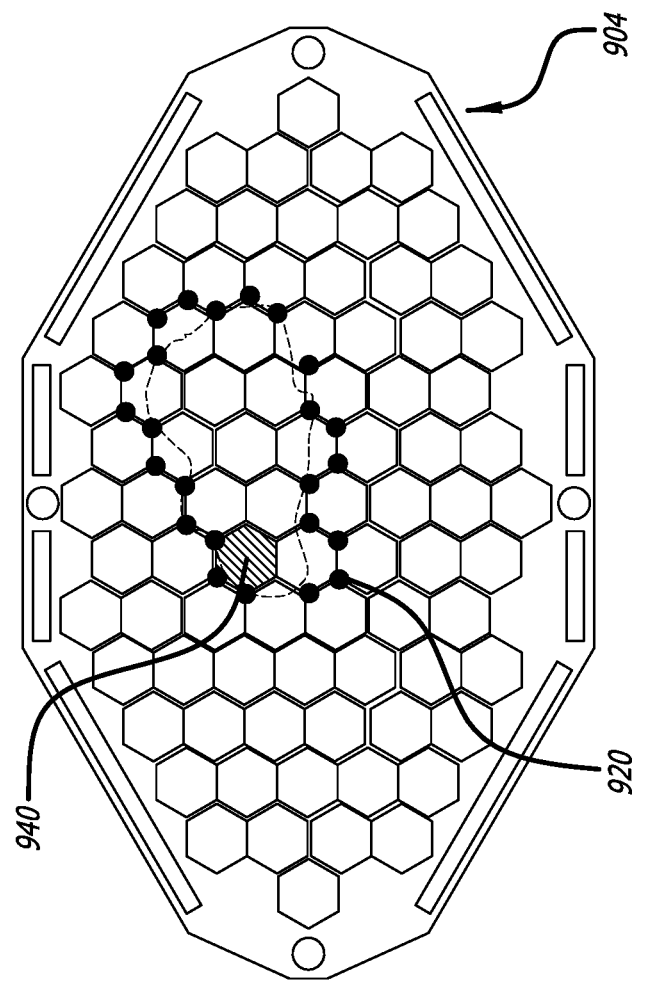
FIG. 9E is a schematic diagram of the treatment head in a third stage of operation according to example aspects of the subject technology.

FIGS. 9A-9F illustrate example stages of treatment operation performed using the x-ray treatment system according to example aspects of the subject technology. Specifically, FIGS. 9A and 9B illustrate an example first stage of treatment operation, FIGS. 9C and 9D illustrate an example second stage of treatment operation, FIGS. 9E and 9F illustrate an example third state of treatment operation according to example aspects of the subject technology.

FIG. 9A is a schematic diagram of a treatment head 904 in the first stage of treatment operation, and FIG. 9B is a schematic diagram of a treatment area (e.g., lesion) 908 of a patient to be treated in the first stage of treatment operation. The treatment head 904 may have the same or similar configuration as the treatment head 200 described in FIG. 2. The steering electromagnet (e.g., steering electromagnet 612 of FIG. 6) of the x-ray treatment system (e.g., systems described in FIGS. 1-7) steers the electron beam to a pixel source cell 916 according to the treatment plan. The pixel source cell 916 is one of the pixel source cells selected to be used to deliver the x-ray photon to the treatment area based on the treatment plan. Fiber optic laser lights 920 are illuminated according to the treatment plan to define the contour of an area to be irradiated by the x-ray photons. As shown in FIG. 9B, the fiber optic laser lights 920 provides laser spots 924 on the patient, and the laser spots 924 mark the contour of the area to be irradiated by the x-ray photons. The contour may encompass the entirety of the treatment area 908. A corresponding x-ray photon flux 918 that was generated by the electron beam transmitted through the pixel source cell 916 strikes a part of the treatment area 908 in the first stage.

FIG. 9C is a schematic diagram of the treatment head 904 in the second stage of treatment operation, and FIG. 9D is a schematic diagram of the treatment area (e.g., lesion) 908 of the patient to be treated in the second stage of treatment operation. In the second stage as shown in FIG. 9C, the steering electromagnet of the x-ray treatment system steers the electron beam to another pixel source cell 930 according to the treatment plan. The pixel source cell 930 is another of the pixel source cells selected to be used to deliver the x-ray photon to the treatment area based on the treatment plan. This results in a corresponding x-ray photon flux 932 striking another part of the lesion 908 as shown in FIG. 9D.

FIG. 9E is a schematic diagram of the treatment head 904 in the third stage of treatment operation, and FIG. 9F is a schematic diagram of the treatment area (e.g., lesion) 908 of the patient to be treated in the third stage of treatment operation. In the third stage as shown in FIG. 9E, the steering electromagnet of the x-ray treatment system steers the electron beam to yet another pixel source cell 940. The pixel source cell 940 is yet another of the pixel source cells selected to be used to deliver the x-ray photon to the treatment area based on the treatment plan. This results in a corresponding x-ray photon flux 942 striking yet another part of the treatment area 908 as shown in FIG. 9F. The process continues until all of the treatment area 908 has been irradiated by x-ray photon flux. The location of the x-ray photon flux can be carefully controlled by the pixel cell source array, with minimal contact with healthy cells, and without the use of a shielding template.

Figure 10A:
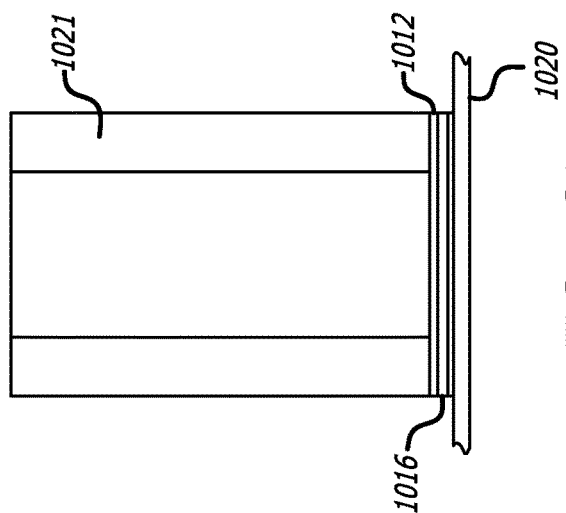
FIG. 10A is a schematic diagram of an example multi-intensity pixel source x-ray hardening filter system according to example aspects of the subject technology.

FIG. 10A shows a schematic diagram of a discrete pixel source cell X-ray hardening multi-filter system 1000 according to example aspects of the subject technology. The x-ray hardening multi-filter system 1000 includes three or more hardening filter layers 1012, 1016, and 1020. The hardening filter layers 1012, 1016, and 1020 may be made of aluminum (Al), or other metallic materials to provide x-ray beam hardening function.

The discrete pixel source cell x-ray hardening multi-filter system 1000 provides an x-ray multi-filtration of three layers or more for each pixel source cell 1021 element in a pixel source cell array (e.g., pixel source cell array 126 of FIG. 1, pixel source cell array 300 of FIG. 3, pixel source cell array 508 of FIG. 5) in a treatment head (e.g., treatment head 200 of FIG. 2, treatment head 504 of FIG. 5, treatment head 904 of FIG. 9) of the x-ray treatment system 100 of the present disclosure. The discrete pixel source cell x-ray hardening multi-filter system 1000 may provide one default filtration and beam hardening layer 1020 for all pixel source cells 1021 in the pixel source cell array of the treatment head. Two or more additional actuated filter layers may be embedded within the pixel source cell 1021 on the far edge of the pixel source cell 1021. The two or more additional actuated filter layers may be of various materials and thicknesses in order to provide different filtering for each pixel source cell, thus providing varying degrees of beam penetration into the targeted treatment area and tissue.

The filter layers 1012, 1016 may each be comprised of one or more segments to allow the filter layers 1012, 1016 to be opened or closed, such as by actuators 1008. Filter layer 1012 may be composed of two segments 1024, 1028 that divide filter layer 1012 in half, as shown in FIGS. 10C and 10E. Filter layer 1016 may be composed of two segments 1032, 1036 that divide filter layer 1012 in half, as shown in FIGS. 10C and 10E.

Figure 10B:
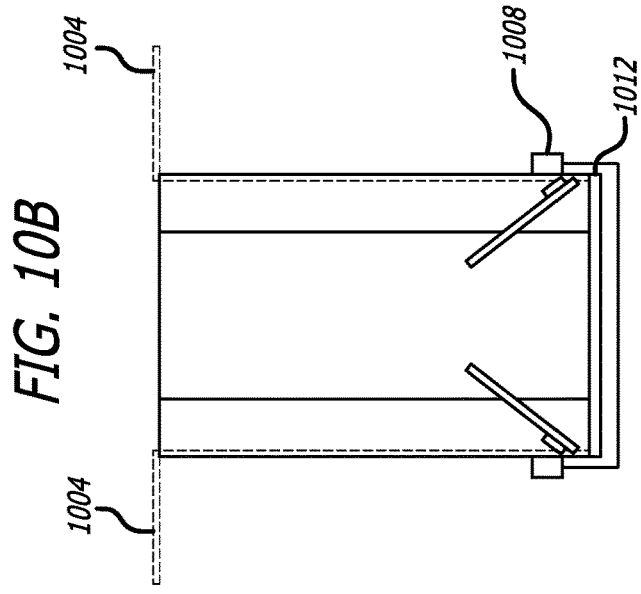
FIG. 10B is a schematic diagram of the multi-intensity pixel source x-ray hardening filter system in a partially opened position according to example aspects of the subject technology.
Figure 10C:
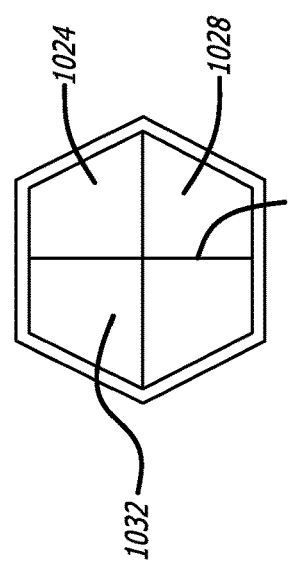
FIG. 10C is a schematic bottom view of the multi-intensity pixel source x-ray hardening filter system according to example aspects of the subject technology.
Figure 10D:
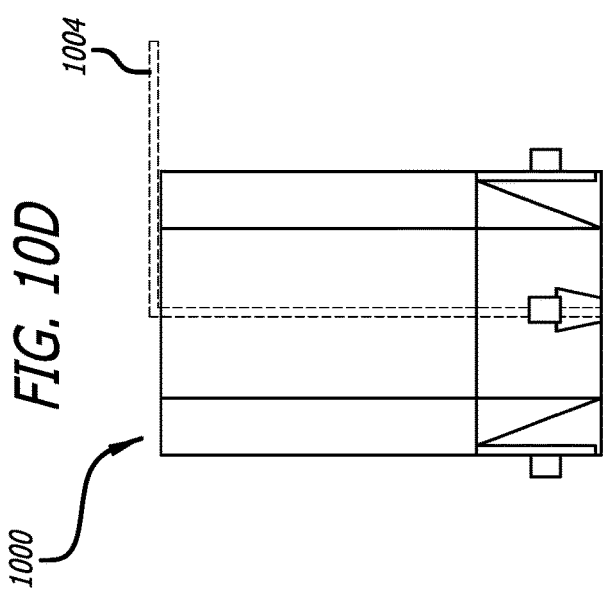
FIG. 10D is a schematic diagram of the multi-intensity pixel source x-ray hardening filter system in a fully opened position according to example aspects of the subject technology.
Figure 10E:
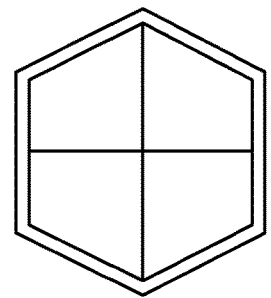
FIG. 10E is a schematic bottom view of the multi-intensity pixel source x-ray hardening filter system according to example aspects of the subject technology.

FIG. 10B shows segments 1032, 1036 of filter layer 1016 in a partially opened position and filter layer 1012 in a closed position at the bottom of pixel source cell 1021. Actuators 1008 may move segments 1032, 1036 between open and closed positions and also vertically within pixel source cell 1021. Actuators 1008 may also be sensors to determine the positions of the segments of filter layers 1012, 1016. Each segment of filter layers 1012, 1016 may have its own actuator 1008. Each actuator 1008 may have a line 1004 to operate the actuator and communicate the position of the segments. FIG. 10D shows all segments 1024, 1028, 1032, 1036 of filter layers 1012, 1016 in open positions near the walls of pixel source cell 1021.

The discrete pixel source cell x-ray hardening multi-filter system 1000 may close the first filter 1016 to add the first filter 1016 to the default filtration layer 1020, thus increasing beam hardening and penetration into the treated tissue or lesion. The discrete pixel source cell x-ray hardening multi-filter system 1000 may also close the third layer 1012 to increase the total beam hardening filter mass and density, thus further increasing beam penetration for each particular pixel source cell 1021 element. This configuration of the discrete pixel source cell x-ray hardening multi-filter system 1000 provides a pixel-by-pixel filtration regulation as required by the treatment plan, and may be may be another embodiment for controlling the intensities of the x-ray photons and the area to which the x-ray photons are delivered to at an individual pixel source cell level.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It may be understood that the described instructions, operations, and systems can generally be integrated together in a single software/hardware product or packaged into multiple software/hardware products.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor may they be interpreted in such a way.

I claim:

1. An x-ray treatment system comprising:
   an electron beam generator configured to generate an electron beam;
   an articulating arm assembly comprising a first end and a second end, the electron beam generator being connected to the first end of the articulating arm assembly;
   an x-ray treatment head disposed on the second end of the articulating arm assembly, wherein the x-ray treatment head is configured to receive the electron beam and wherein the articulating arm assembly is configured to move the x-ray treatment head to a plurality of positions, the x-ray treatment head comprising:
      a pixel source cell array including a plurality of pixel source cells, wherein each of the plurality of pixel source cells comprise:
         side walls defining an x-ray transmissive interior of the pixel source cell, the side walls comprising an x-ray absorptive material; and
         a target element that, when impacted by the electron beam, generates x-ray photon radiation within the x-ray transmissive interior; and
   an electron beam control system comprising a controller configured to:
      receive a treatment plan for a lesion to be treated on a patient;
      select, based on the received treatment plan, one or more pixel source cells out of the plurality of pixel source cells, the one or more pixel source cells depicting a shape of the lesion such that each of one or more edge pixel source cells located at a perimeter of the selected one or more pixel source cells includes a part of a perimeter of the lesion;
      determine, based on the received treatment plan,
         at least one position of the articulating arm assembly from the plurality of positions to position the x-ray treatment head to deliver the x-ray photon radiation to the lesion to be treated; and
         at least one of a direction and intensity of the electron beam to be delivered to each of the selected one or more pixel source cells; and
      transmit data to the electron beam generator, the x-ray treatment head and the articulating arm assembly, the data including:
         the determined at least one position of the articulating arm assembly;
         the selected one or more pixel source cells; and the determined at least one of the direction and the intensity for each of the selected one or more pixel source cells.

2. The x-ray treatment system of claim 1, wherein the articulating arm assembly is a robotic arm comprising a plurality of articulation members configured to be controlled by the pixel source cell array.

3. The x-ray treatment system of claim 2, wherein the plurality of articulation members is configured to allow the movement of the articulating arm assembly about a plurality of orthogonal axes.

4. The x-ray treatment system of claim 3, wherein the robotic arm further comprises a plurality of sensors configured to allow the movement of the articulating arm assembly in relation to a movement of the patient.

5. The x-ray treatment system of claim 4, wherein the plurality of sensors can be configured to measure at least one of force, weight, momentum, and torque.

6. The x-ray treatment system of claim 2, further comprising a hand component disposed on the second end of the articulating arm assembly, the hand component configured to pick-up at least one imaging component configured to acquire image data of the lesion to be treated.

7. The x-ray treatment system of claim 6, wherein the at least one imaging component comprises a plurality of imaging components and wherein the acquire image data comprises a hybrid image of images acquired by the plurality of the imaging components.

8. The x-ray treatment system of claim 6, wherein the at least one imaging component is a confocal imaging head configured to acquire a first plurality of structural and functional images of the lesion at a first depth.

9. The x-ray treatment system of claim 8, wherein the at least one imaging component further comprises a photoacoustic microscopy component configured to obtain a second plurality of structural and functional images of the lesion at a second depth.

10. The x-ray treatment system of claim 1, wherein the target element comprises at least one selected from the group consisting of molybdenum, gold and tungsten.

11. The x-ray treatment system of claim 10, wherein the target element is provided on a substrate.

12. The x-ray treatment system of claim 11, wherein the substrate comprises:
a first substrate; and
a second substrate, wherein the target element is sandwiched between the first substrate and the second substrate.

13. The x-ray treatment system of claim 11, wherein the substrate comprises at least one selected form the group consisting of diamond, beryllium (Be), silicon carbide (SiC), sapphire, aluminum (Al), ceramic alumina ($Al_2O_3$), or boron nitride (BN).

14. The x-ray treatment system of claim 11, wherein the x-ray absorptive material comprises at least one selected from the group consisting of stainless steel, molybdenum (Mo), tungsten (W), and tantalum (Ta).

15. The x-ray treatment system of claim 11, wherein each of the pixel source cells includes the target element within the x-ray transmissive interior.

16. The x-ray treatment system of claim 15, wherein an entire perimeter of the target element provided within the x-ray transmissive interior contacts the side walls of the pixel source cell.

* * * * *